(12) United States Patent
Hirota et al.

(10) Patent No.: US 7,880,038 B2
(45) Date of Patent: Feb. 1, 2011

(54) METAL CATALYST AND ITS USE

(75) Inventors: Masaji Hirota, Niihama (JP); Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 926 days.

(21) Appl. No.: 10/552,664

(22) PCT Filed: Apr. 14, 2004

(86) PCT No.: PCT/JP2004/005312

§ 371 (c)(1),
(2), (4) Date: Oct. 11, 2005

(87) PCT Pub. No.: WO2004/091784

PCT Pub. Date: Oct. 28, 2004

(65) Prior Publication Data

US 2006/0211891 A1    Sep. 21, 2006

(30) Foreign Application Priority Data

Apr. 18, 2003    (JP) ............................. 2003-113778

(51) Int. Cl.
*B01J 27/00* (2006.01)
*B01J 21/04* (2006.01)
*C07C 45/00* (2006.01)

(52) U.S. Cl. .................. 568/471; 502/211; 502/150; 502/155; 502/160; 502/161; 502/208; 502/439; 568/391

(58) Field of Classification Search ............... 502/150, 502/155, 160, 161, 152, 153, 154
See application file for complete search history.

(56) References Cited

U.S. PATENT DOCUMENTS

| | | | | |
|---|---|---|---|---|
| 3,119,875 A | * | 1/1964 | Heinrich et al. | ............ 568/401 |
| 4,562,276 A | * | 12/1985 | Venturello et al. | ............ 556/20 |
| 5,367,032 A | * | 11/1994 | Hancock et al. | .......... 525/333.8 |
| 6,090,956 A | * | 7/2000 | Schulz et al. | ............... 549/529 |
| 6,375,922 B1 | * | 4/2002 | Ishii et al. | ................... 423/591 |
| 7,074,947 B2 | * | 7/2006 | Hirota et al. | ................ 549/531 |
| 2002/0025906 A1 | | 2/2002 | Hagiya et al. | |

FOREIGN PATENT DOCUMENTS

| | | |
|---|---|---|
| EP | 0193368 | 9/1986 |
| EP | 0232742 | 8/1987 |
| EP | 1473290 | 11/2004 |
| JP | 3-236343 A | 10/1991 |
| JP | 6-37423 B2 | 5/1994 |
| JP | 0606976 | 7/1994 |
| JP | 11-349579 * | 12/1999 |
| JP | 11-349579 A | 12/1999 |
| JP | 2002-201147 A | 7/2002 |
| JP | 2003-96016 A | 4/2003 |
| JP | 2003-171333 A | 6/2003 |
| JP | 2003-267905 A | 9/2003 |
| JP | 2004-167474 A | 6/2004 |
| JP | 4013334 B2 * | 11/2007 |
| WO | WO-03/066615 A1 | 8/2003 |

OTHER PUBLICATIONS

WPI World Patent Information Derwent, Abstract of JP5-213919A published Aug. 24, 1993, XP002079746.

* cited by examiner

*Primary Examiner*—Melvin C Mayes
*Assistant Examiner*—Melissa Stalder
(74) *Attorney, Agent, or Firm*—Birch, Stewart, Kolasch & Birch, LLP

(57) ABSTRACT

A metal catalyst obtained by contacting
(A) at least one metal or metal compound selected from
  i) tungsten compounds composed of tungsten and an element of group IIIb, IVb, Vb, or VIb,
  ii) molybdenum compounds composed of molybdenum and an element of group IIIb, IVb, Vb, or VIb, and
  iii) tungsten metal and molybdenum metal;
(B) at least one compound selected from tertiary amine compounds, tertiary amine oxide compounds, nitrogen-containing aromatic compounds and nitrogen-containing aromatic N-oxide compounds;
(C) hydrogen peroxide; and
(D) a phosphate compound, is provided.

3 Claims, No Drawings

METAL CATALYST AND ITS USE

TECHNICAL FIELD

The present invention provides a novel metal catalyst and its use.

BACKGROUND ART

Epoxides are important compounds as various chemicals including resin and the synthetic intermediates for them, and for example, a method for producing cyclooctene oxide by reacting cyclooctene with hydrogen peroxide using tungsten peroxo complex catalyst having dimethyloctadecylamine oxide as a ligand is described (e.g. JP 11-512335 A).

DISCLOSURE OF INVENTION

According to the present invention, it is possible to produce an epoxide, a β-hydroxyhydroperoxide compound or a carbonyl compound from an olefin easily.

That is, the present invention provides a metal catalyst obtained by contacting (A) at least one metal or metal compound selected from i) tungsten compounds composed of tungsten and an element of group IIIb, IVb, Vb, or VIb, ii) molybdenum compounds composed of molybdenum and an element of group IIIb, IVb, Vb, or VIb and iii) tungsten metal and molybdenum metal;

(B) at least one compound selected from tertiary amine compounds, tertiary amine oxide compounds, nitrogen-containing aromatic compounds and nitrogen-containing aromatic N-oxide compounds;

(C) hydrogen peroxide; and (D) a phosphate compound, and its use.

BEST MODE FOR CARRYING OUT THE INVENTION

First, the metal catalyst of the present invention will be illustrated.

Examples of the tungsten compound consisting of tungsten and the above-mentioned element of group IIIb in (A) include tungsten boride. Examples of the tungsten compound consisting of tungsten and the element of group IVb include tungsten carbide and tungsten silicide. Examples of the tungsten compound consisting of tungsten and the element of group Vb include tungsten nitride and tungsten phosphide. Examples of the tungsten compound consisting of tungsten and the element of group VIb include tungsten oxide, tungstic acid, sodium tungstate and tungsten sulfide.

Examples of the molybdenum compound consisting of molybdenum and the element of group IIIb include molybdenum boride. Examples of the molybdenum compound consisting of molybdenum and the element of group IVb include molybdenum carbide and molybdenum silicide. Examples of the molybdenum compound consisting of molybdenum and the element of group Vb include molybdenum nitride and molybdenum phosphide. Examples of the molybdenum compound consisting of molybdenum and the element of group VIb include molybdenum oxide, molybdic acid and molybdenum sulfide.

Among the metal or metal compound, tungsten metal, tungsten boride, sodium tungstate and molybdenum metal are especially preferable. Further, the metal or metal compound may be used alone, or two or more of them may be used by mixing. Furthermore, it is preferred to use the metal or metal compound having a smaller particle size because the metal catalyst can be easily prepared.

Among the compound in (B) group, examples of the tertiary amine include trimethylamine, triethylamine, tri(n-propyl)amine, triisopropylamine, tri(n-butyl)amine, triisobutylamine, tri(n-pentyl)amine, tri(n-hexyl)amine, tri(n-heptyl)amine, tri(n-octyl)amine, tri(n-nonyl)amine, tri(n-decyl)amine, tri(n-dodecyl)amine, tri(n-tetradecyl)amine, tri(n-hexadecyl)amine, tri(n-octadecyl)amine, dimethylethylamine, dimethyl(n-propyl)amine, dimethylisopropylamine, dimethyl(n-butyl)amine, dimethylisobutylamine, dimethyl(n-pentyl)amine, dimethyl(n-hexyl)amine, dimethyl(n-heptyl)amine, dimethyl(n-octyl)amine, dimethyl(n-nonyl)amine, dimethyl(n-decyl)amine, dimethyl(n-undecyl)amine, dimethyl(n-dodecyl)amine, dimethyl(n-tetradecyl)amine, dimethyl(n-hexadecyl)amine, dimethyl(n-octadecyl)amine, methyldiethylamine, di(n-propyl)methylamine, diisopropylmethylamine, di(n-butyl)methylamine, diisobutylmethylamine, di(n-pentyl)methylamine, di(n-hexyl)methylamine, di(n-heptyl)methylamine, di(n-octyl)methylamine, di(n-nonyl)methylamine, di(n-decyl)methylamine, di(n-dodecyl)methylamine, di(n-tetradecyl)methylamine, di(n-hexadecyl)methylamine, di(n-octadecyl)methylamine, dimethylbenzylamine, di(n-butyl)benzylamine, di(n-hexyl)benzylamine, di(n-octyl)benzylamine, di(n-decyl)benzylamine, di(n-dodecyl)benzylamine, di(n-octadecyl)benzylamine, N,N-dimethylaniline, N,N-di(n-butyl)aniline, N,N-di(n-hexyl)aniline, N,N-di(n-octyl)aniline, N,N-di(n-decyl)aniline, N,N-di(n-dodecyl)aniline, N,N-di(n-octadecyl)aniline, N-methylmorpholine, N-(n-butyl)morpholine, N-(n-hexyl)morpholine, N-(n-octyl)morpholine, N-(n-decyl)morpholine, N-(n-dodecyl)morpholine, N-(n-hexadecyl)morpholine, N-(n-octadecyl)morpholine, N-methylpyrrolidine, N-(n-butyl)pyrrolidine, N-(n-hexyl)pyrrolidine, N-(n-octyl)pyrrolidine, N-(n-decyl)pyrrolidine, N-(n-dodecyl)pyrrolidine, N-(n-hexadecyl)pyrrolidine, N-(n-octadecyl)pyrrolidine, N-methylpiperidine, N-(n-butyl)piperidine, N-(n-hexyl)piperidine, N-(n-octyl)piperidine, N-(n-decyl)piperidine, N-(n-dodecyl)piperidine, N-(n-hexadecyl)piperidine and N-(n-octadecyl)piperidine.

Examples of the tertiary amine oxide include the compound in which a nitrogen atom composed of the amino group of the above-mentioned tertiary amine was oxidized such as trimethylamine N-oxide, triethylamine N-oxide and N-methylmorpholine N-oxide. As nitrogen-containing aromatic compound, the compound in which at least one carbon atom selected from carbon atoms composed of the aromatic ring is replaced by a nitrogen atom such as pyridine, 2-methylpyridine, 3-methylpyridine, 4-methylpyridine, 4-ethylpyridine, 4-(n-butyl)pyridine, 4-(1-hexyl)pyridine, 4-(1-hexyl)pyridine, 4-(1-octyl)pyridine, 4-(1-nonyl)pyridine, 4-(5-nonyl)pyridine, 4-(1-decyl)pyridine, 4-dimethylaminopyridine, 4-[di(n-hexyl)amino]pyridine, picolinic acid and pyridine-2,6-dicarboxylic acid is exemplified. As nitrogen-containing aromatic N-oxide compound, the compound in which a nitrogen atom composed of the aromatic ring of the above-mentioned nitrogen-containing aromatic compound is oxidized such as pyridine N-oxide compounds such as pyridine N-oxide is exemplified.

The amount of at least one compound selected from tertiary amine compound, tertiary amine oxide compound, nitrogen-containing aromatic compound and nitrogen-containing aromatic N-oxide compound to be used is usually 0.8 to 3 moles, preferably 0.9 to 1.2 moles per 1 mole of metal compound in terms of the metal.

As hydrogen peroxide (c), an aqueous hydrogen peroxide solution which is an aqueous solution is usually used and a solution of hydrogen peroxide in an organic solvent may be used. It is preferred to use an aqueous hydrogen peroxide solution from the viewpoint of easy handling. The concentration of hydrogen peroxide in an aqueous hydrogen peroxide solution or in a solution of hydrogen peroxide in an organic solvent is not particularly limited, but in view of volume efficacy and safety, the concentration is practically 1 to 60% by weight. As an aqueous hydrogen peroxide solution, a commercially available aqueous hydrogen peroxide solution is usually used as it is, or if necessary, it may be used by appropriately adjusting the concentration by dilution or concentration. In addition, as a solution of hydrogen peroxide in an organic solvent, a solution prepared by extracting an aqueous hydrogen peroxide solution with an organic solvent, or distilling an aqueous hydrogen peroxide solution in the presence of an organic solvent, may be used.

The amount of hydrogen peroxide to be used is usually 3 moles or more, preferably 5 moles or more relative to 1 mole of the metal or metal compound in terms of the metal, and the upper limit of the amount is not particularly defined.

Examples of the phosphate compound (D) include phosphoric acid; alkali metal phosphate such as trisodium phosphate, tripotassium phosphate, disodium hydrogenphosphate, dipotassium hydrogenphosphate, sodium dihydrogenphosphate and potassium dihydrogenphosphate; and alkaline earth metal phosphate such as calcium pyrophosphate and magnesium phosphate. Among them, there are phosphates having hydrates and the hydrates may be used. The amount of the phosphate compound to be used is usually 0.2 mole or more per 1 mole of the metal or metal compound in terms of the metal. Although there is no upper limited particularly, it is usually 1 mole or less.

The metal catalyst of the present invention is prepared by contacting and mixing the above-mentioned catalyst component compounds of (A) to (D). The mixing order is not limited particularly, but it is preferred to mix (A) with (C), followed by adding (D) to the mixture and then adding (B) thereto.

The preparation of the metal catalyst may be carried out without using a solvent and may be carried out in the presence of a solvent. Examples of the solvent include an organic solvent such as an ether solvent such as diethyl ether, methyl tert-butyl ether and tetrahydrofuran; an ester solvent such as ethyl acetate; a tertiary alcohol solvent such as tert-butanol; a nitrile solvent such as acetonitrile and propionitrile; a halogenated hydrocarbon solvent such as dichloromethane; or in a mixture of the organic solvent and water. The preparation temperature of the metal catalyst is usually −10 to 100° C.

By contacting and mixing the above-mentioned four components, the prepared liquid containing the metal catalyst is obtained, and for example, the metal catalyst can be isolated by subjecting the prepared liquid as it is or, after adjusting a pH of the prepared liquid to neutral to acidic, to concentration. Further, the metal catalyst (or as the metal complex) can be also isolated by, if necessary, addition of water and/or a water-insoluble organic solvent to the prepared liquid as it is or after adjusting a pH thereof, followed by extraction and concentration of the resulting organic layer. The metal catalyst is sometimes precipitated in the preparation solution depend on the conditions, and in that case, the metal catalyst may be isolated by filtering the preparation solution. Examples of the water-insoluble organic solvent include, for example, an aromatic hydrocarbon solvent such as toluene and xylene; an ether solvent such as tert-butyl ether; and a halogenated hydrocarbon solvent such as dichloromethane.

Next, use of the obtained metal catalyst will be illustrated. The metal catalyst has an oxidation catalytic activity and by reacting an olefin with hydrogen peroxide in the presence of the above-mentioned metal catalyst, an epoxide, a β-hydroxyhydroperoxide compound or a carbonyl compound can be produced.

First, a method for producing the epoxide by reacting the olefin with hydrogen peroxide using the metal catalyst in a pH range of 2 or more and 4 or less will be illustrated.

The amount of the metal catalyst to be used is usually 0.001 to 0.95 mole, preferably 0.005 to 0.1 mole in terms of the metal per 1 mole of the olefin.

The olefin compound is not particularly limited as far as it is a compound having one or more olefinic carbon-carbon double bond within the molecule. For example, the substituents represented by $R_1$, $R_2$, $R_3$ and $R_4$ bound to two carbon atoms formed the double bond in the formula (1) represented in the following scheme is same or different, and they independently include a substituted or unsubstituted alkyl group, a substituted or unsubstituted aryl group, a substituted or unsubstituted aralkyl group, a substituted silyl group and a halogen atom other than a hydrogen atom.

Examples of the unsubstituted alkyl group include a straight, branched or cyclic C1-10 alkyl group such as a methyl, ethyl, n-propyl, isopropyl, n-butyl, isobutyl, sec-butyl, tert-butyl, n-pentyl, n-hexyl, n-octyl, isooctyl, n-nonyl, n-decyl, cyclopentyl and cyclohexyl group.

Examples of the substituted alkyl group include an alkoxy group (typically, C1-4 alkoxy group) such as a methoxy, ethoxy, n-propoxy, isopropoxy and n-butoxy group; a silyl group substituted with a hydrocarbon radical(s) (for example, the group selected from an alkyl group (C1-4 alkyl group such as a methyl, ethyl, propyl and butyl group) and an aryl group (for example, a phenyl or naphthyl group); further, a straight, branched or cyclic alkyl group (typically, a straight, branched or cyclic C1-10 alkyl group) substituted with a halogen atom such as a fluorine, chlorine and bromine atom.

Examples of the unsubstituted aryl group include a phenyl and naphthyl group. Examples of the substituted aryl group include an aryl group substituted with an alkyl group (for example, C1-10 alkyl group like the above), an alkoxy group (for example, C1-4 alkoxy group like the above), an alkylenedioxy group (for example, a C1-2 alkylenedioxy group such as a methylenedioxy and ethylenedioxy group), a silyl group substituted with a hydrocarbon radical(s) (for example, a silyl group substituted with the group selected from the alkyl and aryl group like the above), a halogen atom like the above, or an acyl group (typically, a C2-4 acyl group) such as an acetyl and propionyl group. Specifically examples thereof include a 2-fluorophenyl, 3-fluorophenyl, 4-fluorophenyl, 2-chlorophenyl, 3-chlorophenyl, 4-chlorophenyl, 2-bromophenyl, 2-methylphenyl, 4-methylphenyl, 4-methoxyphenyl and 4-acetylphenyl group.

As the substituted or unsubstituted aralkyl group, the groups composed of the above-mentioned substituted or unsubstituted alkyl group and the above-mentioned substituted or unsubstituted aryl group is exemplified. Specific examples thereof include a benzyl, phenylethyl, 4-fluorobenzyl, 4-methoxybenzyl and 2-chlorobenzyl group.

Examples of the silyl group substituted with a hydrocarbon radical(s) include a silyl group substituted with a phenyl group(s) or a C1-4 alkyl group(s) such as a trimethylsilyl, triethylsilyl, dimethylphenylsilyl and methyldiphenylsilyl group.

Examples of the halogen atom include a fluorine, chlorine and bromine atom.

Alternatively, the substituent or unsubstituted alkyl groups bonded to carbon atoms composed of the olefinic carbon-carbon double bond may be bonded each other at the terminal together with the carbon atom formed the double bond to form a ring structure. Specific examples of the ring structure include a C4-12 cycloalkane ring such as a cyclobutane ring, a cyclopentane ring, a cyclohexane ring, a cycloheptane ring, a cyclooctane ring, a cyclononane ring, a cyclodecane ring, a cycloundecane ring and a cyclododecane ring, and a cycloalkane ring substituted with an alkyl group (for example, C1-10 alkyl group like the above), an alkoxy group (for example, C1-4 alkoxy group like the above), a silyl group substituted with hydrocarbon radicals (for example, a silyl group substituted with the groups selected from aryl and alkyl groups like the above) or a halogen atom (for example, a fluorine, chlorine, bromine and iodine atom).

As the olefin, for example, a mono-substituted olefin represented by the formula (1a): $R^1HC=CH_2$ in which $R^2$, $R^3$ and $R^4$ are hydrogen atoms in the olefin compound of the formula (1) is exemplified. Meanwhile, in the present description, the mono-substituted olefin is defined including ethylene in which $R^1$ is a hydrogen atom. Specific examples of the mono-substituted olefin include ethylene, propylene, 1-butene, 1-pentene, 4,4-dimethyl-1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 3,3-dimethyl-1-butene, vinylcyclopentane, vinylcyclohexane, allylcyclohexane, styrene, 4-(tert-butyl)styrene, allylbenzene, 4-methoxystyrene, safrole, eugenol and 3,4-dimethoxy-1-allylbenzene.

Alternatively, as the olefin, for example, a di-substituted olefin represented by the formula (1b): $R^1HC=CHR^3$, wherein $R^1$ and $R^3$ represent the substituents like the above other than a hydrogen atom, or the formula (1c): $R^1R^2C=CH_2$, wherein $R^1$, $R^2$ and $R^3$ represent the substituents like the above other than a hydrogen atom, in which $R^2$ and $R^4$ or $R^3$ and $R^4$ are hydrogen atoms in the olefin compound of the formula (1) is exemplified.

Specific examples of the di-substituted olefin include 2-butene, isobutylene, 2-methyl-1-butene, 2-pentene, 2-hexene, 2-methyl-1-hexene, 3-hexene, 2-heptene, 2-methyl-1-heptene, 3-heptene, 2-octene, 3-octene, 4-octene, 2-nonene, 2-methyl-2-nonene, 3-nonene, 4-nonene, 5-decene, 2-methyl-1-undecene, cyclopentene, cyclohexene, 4-methylcyclohexene, cycloheptene, cyclooctene, cyclodecene, cyclododecene, methylenecyclohexane, β-methylstyrene, stilbene, isosafrole, isoeugenol, β-pinene and norbornene.

Further, a tri-substituted olefin represented by the formula (1d): $R^1R^2C=CHR^3$, wherein $R^4$ is a hydrogen atom and $R^1$ to $R^3$ represent the substituents like the above other than a hydrogen atom in the formula (1) is exemplified. Specific examples of the tri-substituted olefin include 2-methyl-2-butene, 2-methyl-2-pentene, 2-methyl-2-hexene, 2,5-dimethyl-2,4-hexadiene, 2-methyl-2-heptene, 1-methylcyclopentene, 1-methylcyclohexene, 1-(tert-butyl)-cyclohexene, 1-isopropylcyclohexene, 2-carene, 3-carene and α-pinene.

A tetra-substituted olefin wherein $R^1$ to $R^4$ represent the substituents like the above other than a hydrogen atom in the formula (1) is exemplified. Specific examples thereof include 2,3-dimethyl-2-butene and 2,3,4-trimethyl-2-pentene.

Among the olefins, there are compounds having geometric isomers or optical isomers. In the present invention, geometric isomers or optically isomers alone may be used and a mixture of geometric isomers or a mixture of optical isomers may be used.

Hydrogen peroxide is usually used as an aqueous solution and a solution of hydrogen peroxide in an organic solvent may be used. It is preferred to use an aqueous hydrogen peroxide solution from the viewpoint of easy handling. The concentration of hydrogen peroxide in an aqueous hydrogen peroxide solution or in a solution in an organic solvent is not particularly limited, but considering volume efficacy and safety, the concentration is practically 1 to 60% by weight. As an aqueous hydrogen peroxide solution, usually, a commercially available aqueous hydrogen peroxide solution may be used as it is, or if necessary, after adjusting the concentration of hydrogen peroxide thereof by dilution, concentration, and the like. A solution of hydrogen peroxide in an organic solvent, for example, can be prepared by means of extraction of an aqueous hydrogen peroxide solution with an organic solvent, or distillation of an aqueous hydrogen peroxide solution in the presence of an organic solvent.

The amount of hydrogen peroxide to be used is usually 0.8 mole or more, preferably 1 mole or more per 1 mole of the olefin. There is no upper limit particularly, but it is usually about 5 moles or less, preferably about 3 moles or less per 1 mole of the olefin.

The reaction of the olefin and hydrogen peroxide may be carried out without using a solvent, and may be carried out in water or an organic solvent. Examples of the organic solvent include an ether solvent such as diethyl ether, methyl tert-butyl ether, tetrahydrofuran and diglyme; an ester solvent such as ethyl acetate; a tertiary alcohol solvent such as tert-butanol; a nitrile solvent such as acetonitrile and propionitrile; and a hydrocarbon solvent such as toluene, benzene, xylene and hexane. The amount of the solvent to be used is not particularly limited.

The reaction is carried out by contacting the metal catalyst, the olefin and hydrogen peroxide in a pH range of 2 or more and 4 or less. Therefore, if necessary, the reaction may be carried out by adjusting the pH of the reaction mixture into the above-mentioned range using acid or alkali.

The reaction temperature is usually −10 to 130° C. The reaction may be usually carried out under ordinary pressure conditions, and may be carried out under reduced pressure conditions or pressurized conditions.

The epoxide is produced with the progress of the reaction, and the progress of the reaction can be confirmed by a conventional analytical means such as gas chromatography, high performance liquid chromatography, thin layer chromatography, NMR and IR.

After completion of the reaction, the desired epoxide can be isolated by subjecting the reaction mixture as it is or, if necessary, after degrading remaining hydrogen peroxide with a reducing agent such as sodium sulfite, to concentration, crystallization, or the like. Further, the epoxide can be also isolated by, if necessary, addition of water and/or a water-insoluble organic solvent to the reaction mixture, followed by extraction and concentration of the resulting organic layer. The isolated epoxide may be further purified by conventional purification means such as distillation, column chromatography and recrystallization.

Examples of thus obtained epoxide include, for example, the epoxide of the following formula (I). Specific examples thereof include ethylene oxide, propylene oxide, 1,2-epoxybutane, 1,2-epoxypentane, 4,4-dimethyl-1,2-epoxypentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxypentadecane, 1,2-epoxyhexadecane, 1,2-epoxyoctadecane, 3,3-dimethyl-1,2-epoxybutane, cyclopentylethylene oxide, cyclohexylethylene oxide, 3-cyclohexyl-1,2- epoxypropane, styrene oxide, 4-(tert-butyl)styrene oxide, 3-phenyl-1,2-epoxypropane, 4-methoxystyrene oxide, safrole oxide, 3-(4-hydroxy-3-methoxyphenyl)-1,2-epoxypropane, 3-(3,4-dimethoxyphenyl)-1,2-epoxypropane, 2,3-epoxybutane, 2-methyl-1,2-epoxypropane, 2-methyl-1,2-epoxybutane, 2,3-epoxypentane, 2,3-epoxyhexane, 2-methyl-1,2-epoxyhexane, 3,4-epoxyhexane, 2,3-epoxyheptane, 3,4-epoxyheptane, 2,3-epoxyoctane, 3,4-epoxyoctane, 4,5-epoxyoctane, 2,3-epoxynonane, 2-methyl-1,2-epoxynonane, 3,4-epoxynonane, 4,5-epoxynonane, 5,6-epoxydecane, 2-methyl-1,2-epoxyundecane, cyclopetene oxide, cyclohexene oxide, 4-methylcyclohexene oxide, cycloheptene oxide, cyclooctene oxide, cyclodecene oxide, cyclododecene oxide, β-methylstyrene oxide, stilbene oxide, isosafrole oxide, 1-(4-hydroxy-3-methoxyphenyl)-1,2-epoxypropane, β-pinene oxide, norbornene oxide, 2-methyl-2,3-epoxybutane, 2-methyl-2,3-epoxypentane, 2-methyl-2,3-epoxyhexane, 2,5-dimethyl-2,3-epoxyhex-4-ene, 2-methyl-2,3-epoxyheptane, 1-methyl-1,2-epoxycyclopentane, 1-methyl-1,2-epoxycyclohexane, 1-(tert-butyl)-1,2-epoxycyclohexane, 1-isopropyl-1,2-epoxycyclohexane, 2-carene oxide, 3-carene oxide, α-pinene oxide, 2,3-dimethyl-2,3-epoxybutane and 2,3,4-trimethyl-2,3-epoxypentane.

Then, a method for producing a β-hydroxyhydroperoxide compound or a carbonyl compound by reacting an olefin with hydrogen peroxide in a pH range of 0 or more and less than 2 in the presence of the metal catalyst will be illustrated.

Examples of the olefin include the compounds as described above. Depending on the reaction conditions and the type of substitution, the β-hydroxyhydroperoxide compound or the carbonyl compound such as the aldehyde, the ketone and the carboxylic acid. The β-hydroxyhydroperoxide compound can be obtained preferably by carrying out the reaction in an organic solvent or under absolute conditions. Examples of the method for carrying out the reaction under absolute conditions include, for example, a method for carrying out in the presence of a dehydrating agent in a reaction system. Examples of the dehydrating agent include anhydrous magnesium sulfate, anhydrous sodium sulfate, boric anhydride, polyphosphoric acid and diphosphorus pentaoxide. As the amount of the dehydrating agent to be used, the amount of the dehydrating agent that can remove water in the reaction system is enough.

The reaction temperature is usually 0 to 200° C. The β-hydroxyhydroperoxide compound and the aldehyde can be obtained preferably when the reaction temperature is less than 65° C. The ketone and the carboxylic acid can be obtained preferably when the reaction temperature is 65° C. or more.

When the mono-substituted olefin is used as the olefin, the β-hydroxyhydroperoxide compound or the carbonyl compound such as the aldehyde and the carboxylic acid preferably are obtained by selecting appropriately the reaction conditions like the above.

For example, the β-hydroxyhydroperoxide compound wherein three groups among $R^1$ to $R^4$ are hydrogen atoms in the formula (II) is obtained mainly by reacting the mono-substituted olefin of the formula (1a) with hydrogen peroxide preferably in the organic solvent or under absolute conditions, more preferably at 0° C. to less than 45° C. in addition to the above-mentioned conditions.

For example, the aldehyde represented by $R^1CHO$ is obtained mainly by reacting the mono-substituted olefin of the formula (1a) with hydrogen peroxide preferably at 45° C. to less than 60° C.

For example, the carboxylic acid represented by $R^1$—COOH is obtained mainly by reacting the mono-substituted olefin of the formula (1a) with hydrogen peroxide preferably at 65° C. or more, more preferably at less than 200° C.

When 1-hexene, for example, is used as the mono-substituted olefin, 2-hydroperoxy-1-hydroxyhexane and/or 1-hydroperoxy-2-hydroxyhexane, pentanal and pentanoic acid are obtained.

For example, the β-hydroxyhydroperoxide compound wherein $R^1$ and $R^2$ are hydrogen atoms in the formula (II) is obtained mainly by reacting the di-substituted terminal olefin of the formula (1c) with hydrogen peroxide preferably in the organic solvent or under absolute conditions, more preferably at 0° C. to less than 45° C. in addition to the above-mentioned conditions.

Also, for example, the ketone represented by the formula (IIIa) is obtained mainly by reacting the di-substituted terminal olefin of the formula (1c) with hydrogen peroxide preferably at 65° C. or more.

When α-methylstyrene, for example, is used as the di-substituted terminal olefin, 2-hydroperoxy-2-phenyl-1-propanol and acetophenone are obtained. When methylenecyclohexane, for example, is used, 1-hydroperoxy-1-hydroxymethylcyclohexane and cyclohexanone are obtained.

When a di-substituted internal olefin is used as the olefin, a β-hydroxyhydroperoxide compound, an aldehyde and a carboxylic acid are obtained.

For example, the β-hydroxyhydroperoxide compound wherein $R^2$ and $R^4$ are hydrogen atoms in the formula (II) is obtained mainly by reacting the di-substituted internal olefin of the formula (1b) with hydrogen peroxide preferably in the organic solvent or under absolute conditions, more preferably at 0° C. to less than 45° C. in addition to the above-mentioned conditions.

Alternatively, for example, the aldehydes represented by $R^1CHO$ and $R^3CHO$ are obtained mainly by reacting the di-substituted internal olefin of the formula (1b) with hydrogen peroxide preferably at 45° C. to less than 65° C.

Alternatively, for example, the carboxylic acids represented by $R^1COOH$ and $R^3COOH$ are obtained mainly by reacting the di-substituted internal olefin of the formula (1b) with hydrogen peroxide preferably at 65° C. or more.

When cyclopentene, for example, is used as the di-substituted internal olefin, 1-hydroperoxy-2-hydroxycyclopentane, glutaraldehyde and glutaric acid are obtained. When 2-hexene, for example, is used, 2-hydroperoxy-3-hydroxyhexane and/or 3-hydroperoxy-2-hydroxyhexane, butanal, butanoic acid, acetaldehyde and acetic acid are obtained.

When a tri-substituted olefin is used as the olefin, the β-hydroxyhydroperoxide compound, the ketone, the aldehyde and the carboxylic acid.

For example, the β-hydroxyhydroperoxide compound wherein $R^4$ is a hydrogen atom in the formula (II) is obtained mainly by reacting the tri-substituted olefin of the formula (1d) with hydrogen peroxide preferably in the organic solvent or under absolute conditions, more preferably at 0° C. to less than 45° C. in addition to the above-mentioned conditions.

Alternatively, for example, the ketone and the aldehyde represented by $R^1R^2C=O$ and $R^3CHO$ are obtained mainly by reacting the tri-substituted olefin of the formula (1d) with hydrogen peroxide preferably at 45° C. to less than 65° C.

Alternatively, for example, the carboxylic acid represented by $R^1R^2C=O$ and $R^3COOH$ are obtained mainly by reacting the tri-substituted olefin of the formula (1d) with hydrogen peroxide preferably at 65° C. or more.

When 2-methyl-2-pentene, for example, is used as the tri-substituted olefin, 2-methyl-2-hydroperoxy-3-hydroxypentane, acetone, propionaldehyde and propionic acid are obtained.

When a tetra-substituted olefin is used as the olefin, the β-hydroxyhydroperoxide compound and the ketone are obtained.

For example, the β-hydroxyhydroperoxide compound of the formula (II) is obtained mainly by reacting the tetra-substituted olefin of the formula (1), provided that wherein $R^1$ to $R^4$ are not hydrogen atoms, with hydrogen peroxide preferably in the organic solvent or under absolute conditions, more preferably at 0° C. to less than 45° C. in addition to the above-mentioned conditions.

Alternatively, for example, the ketones represented by $R^1R^2C=O$ and $R^3R^4C=O$, provided that wherein $R^1$ to $R^4$ are not hydrogen atoms, are obtained mainly by reacting the tetra-substituted olefin of the formula (1) with hydrogen peroxide preferably at 65° C. or more.

When 2,3-dimethyl-2-butene, for example, is used as the tetra-substituted olefin, 2,3-dimethyl-2-hydroperoxy-3-hydroxybutane and acetone are obtained.

Hydrogen peroxide is also usually used as an aqueous solution like the above and a solution of hydrogen peroxide in an organic solvent may be used. The amount of hydrogen peroxide to be used is usually 1 mole or more per 1 mole of the olefin. There is no upper limit particularly, but it is usually 10 moles or less per 1 mole of the olefin.

The amount of the metal complex to be used is usually 0.001 to 0.95 mole, preferably 0.005 to 0.1 mole as the metal per 1 mole of the olefin.

The reaction may be carried out without using a solvent, and may be carried out in water or an organic solvent. Examples of the organic solvent include the solvents as the above.

Since the present reaction is carried out by contacting the olefin and hydrogen peroxide in a pH range of 0 or more to less than 2 in the presence of the metal catalyst, the reaction may be carried out, if necessary, by adjusting the pH of the reaction mixture to the above-mentioned range using acid or alkaline.

The carbonyl compound is produced with the progress of the reaction, and the progress of the reaction can be confirmed by a conventional analytical means such as gas chromatography.

After completion of the reaction, the carbonyl compound can be isolated by subjecting the reaction mixture as it is or, if necessary, after degrading remaining hydrogen peroxide with a reducing agent such as sodium sulfite, to concentration, crystallization, and the like. Further, the carbonyl compound can be also isolated by, if necessary, addition of water and/or a water-insoluble organic solvent to the reaction mixture, followed by extraction and concentration of the resulting organic layer. The isolated carbonyl compound may be further separated or purified by conventional purification means such as distillation, column chromatography and recrystallization.

Examples of thus obtained β-hydroxyhydroperoxide compound include 1-hydroxy-2-hydroperoxyhexane, 2-hydroxy-1-hydroperoxyhexane, 1-hydroxy-2-hydroperoxyheptane, 2-hydroxy-1-hydroperoxyheptane, 1-hydroxy-2-hydroperoxyoctane, 2-hydroxy-1-hydroperoxyoctane, 1-hydroxy-2-hydroperoxydodecane, 2-hydroxy-1-hydroperoxydodecane, 1-hydroxy-2-phenyl-2-hydroperoxyethane, 1-hydroxy-2-(4-methylphenyl)-2-hydroperoxyethane, 1-hydroxy-2-hydroperoxy-3-phenylpropane, 2-hydroxy-1-hydroperoxy-3-phenylpropane, 1-hydroxy-2-hydroperoxy-3-(4-methoxyphenyl)propane and 2-hydroxy-1-hydroperoxy-3-(4-methoxyphenyl)propane.

Examples of thus obtained carbonyl compound include an aldehyde such as formaldehyde, acetaldehyde, propionaldehyde, butylaldehyde, pentylaldehyde, hexylaldehyde, heptylaldehyde, decylaldehyde, undecanylaldehyde, benzaldehyde, 5-oxohexylaldehyde, 2-methyl-5-oxohexylaldehyde, 4-methyl-5-oxohexylaldehyde, 3-methyl-5-oxohexylaldehyde, 2,4-dimethyl-5-oxohexylaldehyde, 3,4-dimethyl-5-oxohexylaldehyde, 2,3-dimethyl-5-oxohexylaldehyde, 2,3,4-trimethyl-5-oxohexylaldehyde, 6-oxoheptylaldehyde, 2-methyl-6-oxoheptylaldehyde, 4-methyl-6-oxoheptylaldehyde, 2,4-dimethyl-6-oxoheptylaldehyde, 2,3-dimethyl-6-oxoheptylaldehyde, 3,4-dimethyl-6-oxoheptylaldehyde, 2,3,4-trimethyl-6-oxoheptylaldehyde, glutaraldehyde, adipaldehyde, heptanedialdehyde, octanedialdehyde, 2-chloroglutaraldehyde, 2-methylglutaraldehyde, 3-methylglutaraldehyde and 2,3-dimethylglutaraldehyde, a ketone such as acetone, methyl ethyl ketone, diethyl ketone, 2-pentanone, 4,4-dimethylpentan-2-one, diethyl ketone, methyl propyl ketone, acetophenone, cyclobutanone, cyclopentanone, cyclohexanone, benzophenone, nopinone, 1,3,3-trimethylindolinone, 2,6-heptanedione, 2,7-octanedione, 1,6-cyclodecanedione, 4-acetoxyacetophenone, 2-methoxy-6-(propan-2-one)acetophenone, 2-carboethoxy-3-methylcyclopentanone and benzophenone, and a carboxylic acid such as formic acid, acetic acid, propionic acid, butanoic acid, pentanoic acid, hexanoic acid, heptanoic acid, benzoic acid, 4-methylbenzoic acid, phenylacetic acid, (4-methoxyphenyl)acetic acid, chloroacetic acid, ethoxyacetic acid, benzyloxyacetic acid, 3,3-dimethyl-2-carbomethoxycyclopropanecarboxylic acid, 3,3-dimethyl-2-carboethoxycyclopropanecarboxylic acid, glutaric acid, adipic acid, pimelic acid, suberic acid, 2-methylglutaric acid, 3-methylglutaric acid, 3-chloroglutaric acid, 2,3-dimethylglutaric acid, 2,4-dimethylglutaric acid, 2-methyladipic acid, 3-methyladipic acid, 2,3-dimethyladipic acid, 2,4-dimethyladipic acid, 3,4-dimethyladipic acid, 2,3,4-trimethylglutaric acid, cyclopentane-1,3-dicarboxylic acid, biphenyl-2,2'-dicarboxylic acid, butane-1,2,3,4-tetracarboxylic acid, 1-(carboxymethyl)cyclopentane-2,3,4-tricarboxylic acid, homophthalic acid and cyclopentane-1,2,3,4-tetracarboxylic acid.

Next, a method for producing a corresponding carbonyl compound by reacting a primary or secondary alcohol and hydrogen peroxide using the metal catalyst of the present invention will be illustrated.

As the primary or secondary alcohol, the formula (2): $R^5R^6CH—OH$, wherein $R^5$ represents a substituted or unsubustituted alkyl group; a substituted or unsubstituted aryl group; a substituted or unsubstituted aralkyl group; or a silyl group substituted with hydrocarbon radicals, and $R^6$ represents a substituted or unsubustituted alkyl group; a substituted or unsubstituted aryl group; a substituted or unsubstituted aralkyl group; a silyl group substituted with hydrocarbon radicals; or a hydrogen atom, are exemplified specifically.

The group represented by $R^5$ or $R^6$ will be illustrated below.

Examples of the unsubstituted alkyl group include a straight, branched or cyclic C1-8 alkyl group such as a methyl, ethyl, n-propyl, isopropyl, n-butyl, isobutyl, sec-butyl, tert-butyl, n-pentyl, n-hexyl, n-octyl, isooctyl, n-nonyl, n-decyl, cyclopentyl and cyclohexyl group. Examples of the substituted alkyl group include an alkyl group substituted with an alkoxy group such as a methoxy, ethoxy, n-propoxy, isopropoxy and n-butoxy group; a silyl group such as a trimethylsilyl group; or a halogen atom such as a fluorine, chlorine and bromine atom.

Specific examples of the substituted alkyl group include a methoxymethyl, ethoxymethyl, methoxyethyl, trimethylsilylmethyl, fluoromethyl, chloromethyl, bromomethyl and trifluoromethyl group.

Examples of the unsubstituted aryl group include a phenyl and naphthyl group. Examples of the substituted aryl group include the aryl group substituted with, for example, the above-mentioned alkyl group; the above-mentioned alkoxy group; the above-mentioned silyl group; the above-mentioned halogen atom; or an acyl group such as an acetyl and propionyl group. Examples of thus substituted aryl group include a 2-fluorophenyl, 3-fluorophenyl, 4-fluorophenyl, 2-chlorophenyl, 3-chlorophenyl, 4-chlorophenyl, 2-bromophenyl, 2-methylphenyl, 4-methylphenyl, 4-methoxyphenyl and 4-acetylphenyl group.

As the substituted or unsubstituted aralkyl group, the group composed of the above-mentioned substituted or unsubstituted alkyl group and the above-mentioned substituted or unsubstituted aryl group. Specific examples thereof include a benzyl, phenylethyl, 4-fluorobenzyl, 4-methoxybenzyl and 2-chlorobenzyl group.

Examples of the silyl group substituted hydrocarbon radicals include a silyl group substituted with the group selected from alkyl groups and aryl groups such as a trimethylsilyl, triethylsilyl, dimethylphenylsilyl and methyldiphenylsilyl group.

Specific examples thereof include a primary alcohol such as ethanol, 1-propanol, 1-butanol, 1-pentanol, 1-hexanol, 1-heptanol, 1-octanol, 1-nonanol, 1-decanol, 2-methyl-1-hexanol, 4-methyl-1-hexanol, 2,2-dimethyl-1-propanol, 1,6-hexanediol, benzyl alcohol, 2-fluorobenzyl alcohol, 3-fluorobenzyl alcohol, 4-fluorobenzyl alcohol, 2-chlorobenzyl alcohol, 3-chlorobenzyl alcohol, 4-chlorobenzyl alcohol, 2-bromobenzyl alcohol, 3-bromobenzyl alcohol, 4-bromobenzyl alcohol, 2-methylbenzyl alcohol, 3-methylbenzyl alcohol, 4-methylbenzyl alcohol, 4-methoxybenzyl alcohol, 2-phenylethanol, 2-(2-fluorophenyl)ethanol, 2-(3-fluorophenyl)ethanol, 2-(4-fluorophenyl)ethanol, 2-(2-chlorophenyl)ethanol, 2-(2-bromophenyl)ethanol, 2-(4-methoxyphenyl)ethanol and 2-(4-acetylphenyl)ethanol.

Further, for example, a secondary alcohol such as 2-propanol, 2-butanol, 2-pentanol, 3-pentanol, 2-hexanol, 3-hexanol, 2-heptanol, 3-heptanol, 4-heptanol, 2-octanol, 3-octanol, 4-octanol, 2-nonanol, 3-nonanol, 4-nonanol, 5-nonanol, 2-decanol, 3-decanol, 4-decanol, 5-decanol, cyclobutanol, cyclopentanol, cyclohexanol, cycloheptanol, cyclooctanol, cyclododecanol, 2-methylcyclohexanol, 3-methylcyclohexanol, 4-methylcyclohexanol, 2-tert-butylcyclohexanol, 3-tert-butylcyclohexanol, 4-tert-butylcyclohexanol, 1-phenylethanol, 1-(2-fluorophenyl)ethanol, 1-(3-fluorophenyl)ethanol, 1-(4-fluorophenyl)ethanol, 1-(2-chlorophenyl)ethanol, 1-(2-bromophenyl)ethanol, 1-(4-methoxyphenyl)ethanol, 1-(4-acetylphenyl)ethanol and α-trimethylsilylbenzyl alcohol is exemplified.

When the primary alcohol (for example, when $R^6$ represents a hydrogen atom in the formula (2)) is used, an aldehyde (for example, $R^5CHO$) and a carboxylic acid (for example, $R^5COOH$) are obtained. When 1-butanol is used as the primary alcohol for example, butylaldehyde and/or butanoic acid are obtained.

When the secondary alcohol (for example, when $R^6$ is not a hydrogen atom in the formula (2)) is used, a ketone (for example, $R^5COR^6$) is obtained. When 1-phenylethanol is used as the secondary alcohol for example, acetophenone is obtained.

Hydrogen peroxide is also usually used as an aqueous solution like the above and a solution of hydrogen peroxide in an organic solvent may be used. The amount of hydrogen peroxide to be used may be set for to the alcohol to be used and the desired carbonyl compound as below.

When the primary alcohol is used and the aldehyde is desired, the amount of hydrogen peroxide to be used is usually 0.9 to 1.5 moles per 1 mole of the alcohol. When the primary alcohol is used and the carboxylic acid is desired, the amount of hydrogen peroxide to be used is usually 1.5 moles or more per 1 mole of the alcohol. There is no upper limit particularly, but it is usually 10 moles or less per 1 mole of the alcohol.

When the secondary alcohol is used and the ketone is desired, the amount of hydrogen peroxide to be used is usually 0.9 mole or more per 1 mole of the alcohol. There is no upper limit particularly, but it is usually 10 moles or less per 1 mole of the alcohol.

The amount of the metal catalyst to be used is usually about 0.001 to 0.95 mole, preferably about 0.005 to 0.1 mole as the metal per 1 mole of the primary or secondary alcohol.

The reaction may be carried out without using a solvent, and may be carried out in water or an organic solvent. Examples of the organic solvent include the solvents as same as those exemplified as the solvents used for producing the epoxides.

The present reaction is carried out by contacting the metal catalyst, the primary or secondary alcohol and hydrogen peroxide. The mixing order is not particularly limited.

The reaction temperature is usually in a range of about 0 to 200° C.

A carbonyl compound is produced with the progress of the reaction, and the progress of the reaction can be also confirmed by a conventional analytical means such as gas chromatography like the above.

After completion of the reaction, the carbonyl compound can be isolated by subjecting the reaction mixture as it is or, if necessary, after degrading remaining hydrogen peroxide with a reducing agent such as sodium sulfite, to concentration, crystallization, and the like. Further, the carbonyl compound can be also isolated by, if necessary, addition of water and/or a water-insoluble organic solvent to the reaction mixture, followed by extraction and concentration of the resulting organic layer. The isolated carbonyl compound may be separated or further purified, if necessary, by conventional means such as distillation, column chromatography and recrystallization.

Examples of thus obtained carbonyl compound include acetaldehyde, propionaldehyde, butylaldehyde, pentylaldehyde, hexylaldehyde, heptylaldehyde, octylaldehyde, nonylaldehyde, decylaldehyde, 2-methyl-1-hexylaldehyde, 2,2-dimethyl-1-propionaldehyde, adipaldehyde, benzaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2-bromobenzaldehyde, 3-bromobenzaldehyde, 4-bromobenzaldehyde, 2-methylbenzaldehyde, 3-methylbenzaldehyde, 4-methylbenzaldehyde, 4-methoxybenzaldehyde, 2-phenylacetaldehyde, 2-(2-fluorophenyl)acetaldehyde, 2-(3-fluorophenyl)acetaldehyde, 2-(4-fluorophenyl)acetaldehyde, 2-(2-chlorophenyl)acetaldehyde, 2-(2-bromophenyl)acetaldehyde, 2-(4-methoxyphenyl)acetaldehyde and 2-(4-acetylphenyl)acetaldehyde.

Examples of the carboxylic acid include, acetic acid, propionic acid, butanoic acid, pentanoic acid, hexanoic acid, heptanoic acid, octanoic acid, nonanoic acid, decanoic acid, 2-methyl-1-hexanoic acid, 4-methyl-1-hexanoic acid, 2,2-dimethyl-1-propionic acid, adipinic acid, benzoic acid, 2-fluorobenzoic acid, 3-fluorobenzoic acid, 4-fluorobenzoic acid, 2-chlorobenzoic acid, 3-chlorobenzoic acid, 4-chlorobenzoic acid, 2-bromobenzoic acid, 3-bromobenzoic acid, 4-bromobenzoic acid, 2-methylbenzoic acid, 3-methylbenzoic acid, 4-methylbenzoic acid, 4-methoxybenzoic acid, phenylacetic acid, (2-fluorophenyl)acetic acid, (3-fluorophenyl)acetic acid, (4-fluorophenyl)acetic acid, (2-chlorophenyl)acetic acid, (2-bromophenyl)acetic acid, (4-methoxyphenyl)acetic acid and (4-acetylphenyl)acetic acid.

Examples of the ketone include acetone, 2-butanone, 2-pentanone, 3-pentanone, 2-hexanone, 3-hexanone, 2-heptanone, 3-heptanone, 4-heptanone, 2-octanone, 3-octanone, 4-octanone, 2-nonanone, 3-nonanone, 4-nonanone, 5-nonanone, 2-decanone, 3-decanone, 4-decanone, 5-decanone, cyclobutanone, cyclopentanone, cyclohexanone, cycloheptanone, cyclooctanone, cyclododecanone, 2-methylcyclohexanone, 3-methylcyclohexanone, 4-methylcyclohexanone, 2-tert-butylcyclohexanone, 3-tert-butylcyclohexanone, 4-tert-butylcyclohexanone, acetophenone, o-fluoroacetophenone, m-fluoroacetophenone, p-fluoroacetophenone, o-chloroacetophenone, o-bromoacetophenone, o-methoxyacetophenone, p-methoxyacetophenone, p-methoxyacetophenone and benzoyltrimethylsilane.

A part of the embodiments of the method for producing of the present invention will be illustrated as scheme below.

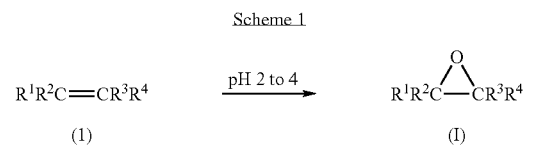

Scheme 1

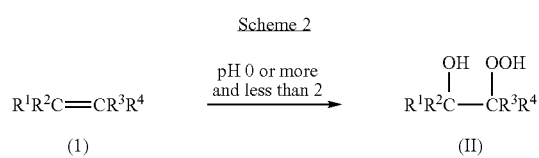

Scheme 2

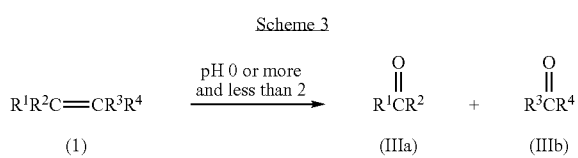

Scheme 3

EXAMPLES

The following Examples further illustrate the present invention in detail, but the present invention is not limited by these Examples. Gas chromatography was used for analysis.

Example 1

Into a 50 mL round-bottomed flask equipped with a reflux condenser, 0.92 g of a tungsten metal powder and 3.96 g of a 30% by weight aqueous hydrogen peroxide were charged at room temperature, and the mixture was stirred and maintained for 15 minutes to obtain a clear and colorless homogeneous solution. To the solution, 0.49 g of phosphoric acid was added and the resulting solution was stirred and maintained at room temperature for 2 hours. 2.92 g of tri(n-dodecyl)amine and 8 mL of dichloromethane were added thereto and the resulting solution was stirred and maintained at room temperature for 4 hours. Then, the resulting solution was subjected to separation treatment and the obtained organic layer was concentrated to obtain 4.02 g of yellow wax solid tungsten complex. Yield 97% (based on the tungsten metal).

$^1$H-NMR(solvent: CDCl$_3$, based on TMS, unit: ppm) δ 0.88 (t, 9H, J=7.0 Hz), 1.25-1.30 (m, 54H), 1.73 (br, 6H), 3.59 (br, 6H)

$^{13}$C-NMR(solvent: CDCl$_3$, based on TMS, unit: ppm) δ 14.1, 22.7, 22.9, 26.1, 29.4, 29.7, 31.9, 63.6

IR(neat, unit: cm$^{-1}$) 2956, 2921, 2871, 2853, 1546, 1466, 1403, 1378, 1315, 1262, 1072, 1035, 941, 888, 848, 767, 751, 721, 678, 644 elementary analysis value: C, 54.4; H, 9.8; N, 1.6; P, 0.95.

Example 2

Into a 50 mL round-bottomed flask equipped with a reflux condenser, 0.88 g of a tungsten metal powder, 4 g of water and 3.96 g of a 30% by weight aqueous hydrogen peroxide were charged at room temperature, and the mixture was stirred and maintained for 15 minutes to obtain a clear and colorless homogeneous solution. To the solution, 0.56 g of phosphoric acid was added and the resulting solution was stirred and maintained at room temperature for 2 hours. 2.88 g of tri(n-dodecyl)amine N-oxide and 10 mL of dichloromethane were added thereto and the resulting solution was stirred and maintained at room temperature for 4 hours. Then, the resulting solution was subjected to separation treatment and the obtained organic layer was concentrated to obtain 4.00 g of yellow wax solid tungsten complex. Yield 100% (based on the tungsten metal).

$^1$H-NMR(solvent: CDCl$_3$, based on TMS, unit: ppm) δ 0.88 (t, 9H, J=7.0 Hz), 1.25-1.30 (m, 54H), 1.73 (br, 6H), 3.59 (br, 6H)

$^{13}$C-NMR(solvent: CDCl$_3$, based on TMS, unit: ppm) δ 14.1, 22.7, 22.9, 26.1, 29.4, 29.7, 31.9, 63.6

IR(neat, unit: cm$^{-1}$) 2956, 2921, 2871, 2853, 1466, 1378, 1078, 1036, 944, 888, 848, 772, 721, 678 elementary analysis value: C, 54.4; H, 9.7; N, 1.7; P, 1.41.

Example 3

Into a 50 mL round-bottomed flask equipped with a reflux condenser, 0.92 g of a tungsten metal powder, 4 g of water and 3.96 g of a 30% by weight aqueous hydrogen peroxide were charged at room temperature, and the mixture was stirred and maintained for 15 minutes to obtain a clear and colorless homogeneous solution. To the solution, 0.58 g of phosphoric acid was added and the resulting solution was stirred and maintained at room temperature for 2 hours. 1.77 g of tri(n-octyl)amine and 10 mL of diethyl ether were added thereto and the resulting solution was stirred and maintained at room temperature for 4 hours. Then, the resulting solution was subjected to separation treatment and the obtained organic layer was concentrated to obtain 3.20 g of yellow wax solid tungsten complex. Yield 99% (based on the tungsten metal).

$^1$H-NMR(solvent: CDCl$_3$, based on TMS, unit: ppm) δ 0.89 (t, 9H, J=7.0 Hz), 1.2-1.25 (m, 30H), 1.72 (br, 6H), 3.10 (br, 2H), 3.57 (br, 4H), 6.0 (br, 2H)

$^{13}$C-NMR(solvent: CDCl$_3$, based on TMS, unit: ppm) δ 14.0, 22.6, 23.2, 26.0, 26.6, 28.9, 29.1, 29.2, 31.7, 52.8, 63.9

IR(neat, unit: cm$^{-1}$) 2956, 2926, 2856, 1458, 1376, 1086, 1034, 949, 891, 845, 723, 677, 647 elementary analysis value: C, 42.3; H, 7.9; N, 2.0; P, 1.82.

Example 4

Into a 100 mL Schlenk tube equipped with a reflux condenser, 0.66 g of the tungsten complex obtained in the above-mentioned Example 1, 9.6 g of a 30% by weight aqueous hydrogen peroxide, 0.1 g of a 20% by weight aqueous sodium hydroxide and a toluene solution containing 2.2 g of 1-octene (used 4 mL of toluene) were charged at room temperature, and the mixture was stirred for 6 hours at an inner temperature of 90° C. to effect reaction. A pH value of the reaction mixture was about 3.5. After completion of the reaction, the reaction mixture was cooled to room temperature and subjected to separation treatment to obtain an organic layer containing 1,2-epoxyoctane. Yield of 1,2-epoxyoctane was 84% (based on 1-octene).

Example 5

Into a 100 mL Schlenk tube equipped with a reflux condenser, 0.66 g of the tungsten complex obtained in the above-mentioned Example 1, 9.6 g of a 30% by weight aqueous hydrogen peroxide and a toluene solution containing 2.2 g of 1-octene (used 4 mL of toluene) were charged at room temperature, and the mixture was stirred for 6 hours at an inner temperature of 90° C. to effect reaction. A pH value of the reaction mixture was about 1.7. After completion of the reaction, the reaction mixture was cooled to room temperature and subjected to separation treatment to obtain an organic layer containing heptanoic acid. Yield of heptanoic acid was 84% (based on 1-octene).

Example 6

Into a 50 mL flask equipped with a reflux condenser, 66 mg of the tungsten complex obtained in the above-mentioned Example 2, 5.7 g of a 30% by weight aqueous hydrogen peroxide and 980 mg of 1-heptene were charged at room temperature, and the mixture was stirred for 6 hours at an inner temperature of 90° C. to effect reaction. After completion of the reaction, the reaction mixture was cooled to room temperature and, 10 mL of diethyl ether was added thereto. The reaction mixture was subjected to separation treatment to obtain an organic layer containing hexanoic acid. Yield of hexanoic acid was 60% (based on 1-heptene). 1-heptene was recovered in 35%.

Example 7

Into a 50 mL flask equipped with a reflux condenser, 66 mg of the tungsten complex obtained in the above-mentioned Example 2, 3.4 g of a 30% by weight aqueous hydrogen peroxide and 1.08 g of benzyl alcohol were charged at room temperature, and the mixture was stirred for 6 hours at an inner temperature of 90° C. to effect reaction. After completion of the reaction, the reaction mixture was cooled to room temperature and 10 mL of toluene was added thereto. The reaction mixture was subjected to separation treatment to obtain an organic layer containing benzoic acid. Yield of benzoic acid was 94% (based on benzyl alcohol).

Example 8

Into a 50 mL flask equipped with a reflux condenser, 70 mg of the tungsten complex obtained in the above-mentioned Example 2, 1.37 g of a 30% by weight aqueous hydrogen peroxide and 1.31 g of benzyl alcohol were charged at room temperature, and the mixture was stirred for 2 hours at an inner temperature of 80° C. to effect reaction. After completion of the reaction, the reaction mixture was cooled to room temperature and 10 mL of toluene was added thereto. The reaction mixture was subjected to separation treatment to obtain an organic layer containing benzaldehyde. Yield of benzaldehyde was 89% (based on benzyl alcohol). Benzoic acid was formed as by-product in 10%.

Example 9

Into a 50 mL flask equipped with a reflux condenser, 60 mg of the tungsten complex obtained in the above-mentioned Example 3, 3.4 g of a 30% by weight aqueous hydrogen peroxide and 1.02 g of 1-hexanol were charged at room temperature, and the mixture was stirred for 6 hours at an inner temperature of 90° C. to effect reaction. After completion of the reaction, the reaction mixture was cooled to room temperature and 10 mL of diethyl ether was added thereto. The reaction mixture was subjected to separation treatment to obtain an organic layer containing hexanoic acid. Yield of hexanoic acid was 89% (based on 1-hexanol).

Example 10

Into a 50 mL flask equipped with a reflux condenser, 60 mg of the tungsten complex obtained in the above-mentioned Example 3, 3.4 g of a 30% by weight aqueous hydrogen peroxide and 1.22 g of 1-phenethyl alcohol were charged at room temperature, and the mixture was stirred for 6 hours at an inner temperature of 90° C. to effect reaction. After completion of the reaction, the reaction mixture was cooled to room temperature and 10 mL of toluene was added thereto. The reaction mixture was subjected to separation treatment to obtain an organic layer containing acetophenone. Yield of acetophenone was 99% (based on 1-phenethyl alcohol).

Example 11

Into a 50 mL round-bottomed flask equipped with a reflux condenser, 1.58 g of sodium tungstate dihydrate, 4 g of water and 3.96 g of a 30% by weight aqueous hydrogen peroxide were charged at room temperature, and the mixture was stirred and maintained for 15 minutes to obtain a clear and colorless homogeneous solution. To the solution, 1.66 g of phosphoric acid was added and the resulting solution was stirred and maintained at room temperature for 2 hours. 1.77 g of tri(n-octyl)amine and 10 mL of diethyl ether were added thereto and the resulting solution was stirred and maintained at room temperature for 4 hours. Then, the resulting solution was subjected to separation treatment and the obtained organic layer was concentrated to obtain 2.8 g of yellow wax solid tungsten complex. Yield 88% (based on tungsten).

$^1$H-NMR(solvent: $CDCl_3$, based on TMS, unit: ppm) δ 0.89 (t, 9H, J=7.0 Hz), 1.2-1.5 (m, 30H), 1.73 (br, 6H), 3.10 (br, 2H), 3.55 (br, 4H), 6.0 (br, 2H)

$^{13}$C-NMR(solvent: $CDCl_3$, based on TMS, unit: ppm) δ 14.0, 22.6, 23.2, 26.0, 26.6, 28.9, 29.1, 29.2, 31.7, 52.6, 63.8 elementary analysis value: C, 45.6; H, 8.1; N, 2.2; P, 1.73.

Example 12

Into a 50 mL flask equipped with a reflux condenser, 60 mg of the tungsten complex obtained in the above-mentioned Example 11, 3.4 g of a 30% by weight aqueous hydrogen peroxide and 1.08 g of benzyl alcohol were charged at room temperature, and the mixture was stirred for 6 hours at an inner temperature of 90° C. to effect reaction. After completion of the reaction, the reaction mixture was cooled to room temperature and 10 mL of toluene was added thereto. The reaction mixture was subjected to separation treatment to obtain an organic layer containing benzoic acid. Yield of benzoic acid was 94% (based on benzyl alcohol).

Comparative Example 1

According a similar manner as that of Example 1, 4.13 g of pale yellow wax solid tungsten complex was obtained except that 0.49 g of phosphoric acid was not used.

IR(neat, unit: $cm^{-1}$) 2956, 2922, 2853, 1550, 1466, 1378, 1045, 977, 958, 876, 815, 782, 720

INDUSTRIAL APPLICABILITY

According to the present invention, A metal catalyst is prepared by contacting (A) at least one metal or metal compound selected from the group consisting of i) tungsten compounds composed of tungsten and an element of group IIIb, IVb, Vb, or VIb, ii) molybdenum compounds composed of molybdenum and an element of group IIIb, IVb, Vb, or VIb; (B) at least one compound selected from the group consisting of tertiary amine compounds, tertiary amine oxide compounds, nitrogen-containing aromatic compounds and nitrogen-containing aromatic N-oxide compounds; (C) hydrogen peroxide; and (D) a phosphate compound. Since an epoxide is obtained from olefin and hydrogen peroxide using the metal catalyst without using a solvent having problems in the viewpoint of environment and occupational safety and health such as chloroform as reaction solvent, it is industrially advantageous. Further, since a carbonyl compound such as aldehyde wherein a carbon-carbon bond of an olefin is broken oxidatively or a β-hydroxyhydroperoxide compound is obtained, it is useful industrially in this viewpoint, too.

The invention claimed is:

1. A process for producing a β-hydroxyhydroperoxide compound or a carbonyl compound, which comprises: contacting
   (A) at least one metal or metal compound selected from
   i) tungsten compounds composed of tungsten and an element of group IIIb, IVb, Vb, or VIb,
   ii) molybdenum compounds composed of molybdenum and an element of group IIIb, IVb, Vb, or VIb, and
   iii) tungsten metal and molybdenum metal;
   (B) at least one compound selected from tertiary amine oxide compounds and nitrogen-containing aromatic N-oxide compounds;
   (C) hydrogen peroxide; and
   (D) a phosphate compound,
   to obtain a metal catalyst and then reacting an olefin with hydrogen peroxide in the pH range of 0 or more and less than 2 in the presence of said metal catalyst, wherein the carbonyl compound is produced by oxidatively breaking a carbon-carbon bond of the olefin.

2. A process for producing a carbonyl compound, which comprises: contacting
   (A) at least one metal or metal compound selected from
   i) tungsten compounds composed of tungsten and an element of group IIIb, IVb, Vb, or VIb,
   ii) molybdenum compounds composed of molybdenum and an element of group IIIb, IVb, Vb, or VIb, and
   iii) tungsten metal and molybdenum metal;
   (B) at least one compound selected from tertiary amine oxide compounds and nitrogen-containing aromatic N-oxide compounds;
   (C) hydrogen peroxide; and
   (D) a phosphate compound,
   to obtain a metal catalyst and then reacting a primary alcohol with hydrogen peroxide in the presence of said metal catalyst, wherein the carbonyl compound is an aldehyde and the amount of hydrogen peroxide to be used is 0.9 to 1.5 moles per 1 mole of primary alcohol.

3. A process for producing a carbonyl compound, which comprises: contacting
   (A) at least one metal or metal compound selected from
   i) tungsten compounds composed of tungsten and an element of group IIIb, IVb, Vb, or VIb,
   ii) molybdenum compounds composed of molybdenum and an element of group IIIb, IVb, Vb, or VIb, and
   iii) tungsten metal and molybdenum metal;
   (B) at least one compound selected from tertiary amine oxide compounds and nitrogen-containing aromatic N-oxide compounds;
   (C) hydrogen peroxide; and
   (D) a phosphate compound,
   to obtain a metal catalyst and then reacting a primary alcohol with hydrogen peroxide in the presence of said metal catalyst, wherein the carbonyl compound is a carboxylic acid and the amount of hydrogen peroxide to be used is 1.5 moles or more per 1 mole of primary alcohol.

* * * * *